US00RE39086E

(19) United States
(12) Reissued Patent
Carruthers et al.

(10) Patent Number: US RE39,086 E
(45) Date of Reissued Patent: May 2, 2006

(54) COSMETIC USE OF BOTULINUM TOXIN FOR TREATMENT OF DOWNTURNED MOUTH

(75) Inventors: Jean D. A. Carruthers, Vancouver (CA); Alastair Carruthers, Vancouver (CA)

(73) Assignee: Allergan, Inc., Irvine, CA (US)

(21) Appl. No.: 10/802,381

(22) Filed: Mar. 17, 2004

Related U.S. Patent Documents

Reissue of:
(64) Patent No.: 6,358,917
Issued: Mar. 19, 2002
Appl. No.: 09/382,002
Filed: Aug. 24, 1999

(51) Int. Cl.
*A61K 38/16* (2006.01)
*A61M 31/00* (2006.01)

(52) U.S. Cl. ..... 514/2; 514/844; 514/906; 604/511; 604/522

(58) Field of Classification Search ..... 514/2, 514/8, 12, 21, 844, 906; 530/350, 395, 825; 604/506, 511, 522; 128/898; 424/239.1, 401
See application file for complete search history.

(56) References Cited

U.S. PATENT DOCUMENTS 5,401,243 A * 3/1995 Borodic ..... 604/511
5,750,141 A * 5/1998 Roberts et al. ..... 424/449
6,001,088 A * 12/1999 Roberts et al. ..... 604/501

OTHER PUBLICATIONS

Hoefflin (1998). "Anatomy of the Platysma and Lip Depressor Muscles". *Dermatol. Surg.*, vol. 24: 1225–1231.*
Bikhazi et al. "Refinement in the Rehabilitation of the Paralyzed Face . . . " Otol. Head Neck Surg. vol. 117, No. 4, pp. 303–307, Oct. 1997.*
Garcia et al. "Cosmetic Denervation of the Muscles . . . " Dermatol. Surg. vol. 22, pp. 39–43, 1996.*
Guyuron et al. "Aesthetic Indications for Botulinum . . . " Plast. Reconstr. Surg. vol. 93, No. 5, pp. 913–918, Apr. 1994.*
Song. "Botulinum Toxin Type A Injection . . . " Annals Pharmacotherapy. vol. 32, pp. 1365–1367, Dec. 1998.*
Wieder et al. "Understanding Botulinum Toxin" Dermatol. Surg. vol. 24, pp. 1172–1174, 1998.*
Armstrong et al. (1996). "Treatment of facial synkinesis and facial asymmetry with botulinum toxin type A following facial nerve palsy" Clin. Otolaryngol., vol. 21: 15–20.*
Brandt et al. (1998). "Cosmetic Use of Botulinum A exotoxin for the Aging Neck" Dermatol. Surg., vol. 24: 1232–1234.*
Carruthers, (1999). "Botulinum Toxin for Midfacial Defects" 57th Annual Meeting American Academy of Dermatology, pp. 21–22.*
Carruthers et al. (1998). "The Adjunctive Usage of Botulinum Toxin" Dermatol. Surg., vol. 24: 1244–1247.*
Carruthers et al. (1998). "Clinical Indications and Injection Technique for the Cosmetic Use of Botulinum A Exotoxin" Dermatol. Surg. vol. 24: 1189–1194.*
Carruthers et al. (1998). "History of the Cosmetic Use of Botulinum A Exotoxin" Dermatol. Surg. vol. 24: 1168–1170.*
Carruthers et al. (1996). "Botulinum A exotoxin in clinical ophthalmology" Can. J. Ophthalmol., vol. 31(7): 389–400.*

(Continued)

*Primary Examiner*—Jeffrey Edwin Russel
(74) *Attorney, Agent, or Firm*—Stout, Uxa, Buyan & Mullins, LLP; Frank J. Uxa; Greg S. Hollrigel

(57) ABSTRACT

This invention provides the use of Botulinum toxin (BTX) to cause paralysis of a depressor anguli oris (DAO) musculature in a patient to alleviate downturn at corners of the patient's mouth.

26 Claims, 2 Drawing Sheets

OTHER PUBLICATIONS

Carruthers et al. (1994). "Botulinum Toxin in the Treatment of Glabellar Frown Lines and Other Facial Wrinkles" In Therapy with Botulinum Toxin (Jankovic et al. eds.) Ch. 46: 577–595.*

Klein (1999). "Botulinum Toxin for the Aging Face" 57th Annual Meeting American Academy of Dermatology, pp. 20–20C.*

Sabbaugh, "Extending the use of botulinum toxin for aesthetic indications",Eye World, 3(6):37–8, (Jun. 1998).

Blitzer et al., "Botulinum toxin for the treatment of hyperfunctional lines of the face", Arch Otolaryngol–Head Neck Sug. Sep. 1993; 119(9):1018–22.

Foster, "Botulinum toxin can smooth out the wrinkles", Ophthalmology Times, Apr., 1997.

Abstract—Klein, Using obtulinum toxin to treat facial and periocular wrinkles, Ocul Surg. News Oct. 1992:10(20):166–7.

* cited by examiner

COSMETIC USE OF BOTULINUM TOXIN FOR TREATMENT OF DOWNTURNED MOUTH

Matter enclosed in heavy brackets [ ] appears in the original patent but forms no part of this reissue specification; matter printed in italics indicates the additions made by reissue.

FIELD OF THE INVENTION

This invention relates to cosmetic uses of neuroparalytic toxins.

BACKGROUND OF THE INVENTION

Marionette lines are cosmetic defects of the human face often caused by a loss of dermal collagen in the lower lips and chin area as a result of aging. These lines are usually accompanied by a downturn at the corners of the mouth, producing a "sad" appearance, hence the term "sad mouth". In this condition, the horizontal symmetry of the mouth is offset in a downward or inferior direction as a result of the downturn at the corners of the mouth.

Some facial wrinkles and unsightly facial expressions are due to overactivity of the underlying facial musculature. Neuroparalytic toxins have been used for treatment of wrinkles and in other treatments for facial rejuvenation. A toxin capable of blocking neuromuscular activity is administered to a facial muscle responsible for the facial defect or lesion. Resulting paralysis of the facial muscle alleviates the facial defect. The preferred toxin for cosmetic use is Botulinum toxin (BTX).

BTX, produced by the bacterium Clostridium botulinum reversibly paralyzes striated muscle when administered in sub-lethal doses. BTX has been used in the treatment in a number of neuromuscular disorders and conditions involving muscular spasm including various forms of dystonia, hemifacial spasm, tremor, spasticity (e.g. resulting from Multiple sclerosis), anal fissures and various ophthalmologic conditions (c.f. A. Carruthers et al (1996), Botulinum A Exotoxin Use in Clinical Dermatology; Journal of the American Academy of Dermatology 34: 788–797).

BTX is a generic term covering a family of toxins produced by C. botulinum comprising up to eight serologically distinct forms (A, B, $C_1$, $C_2$, D, E, F and G). These toxins which are among the most powerful neuroparalytic agents known (c.f. Melling, J. et al (1988) Clostridium Botulinum: Nature and Preparation for Clinical Use; Eye 2: 16–23). Serotypes A, B and F are the most potent. The mode of action is to inhibit the release of acetylcholine by the presynaptic nerve.

BTX-A serotype is available commercially under the trademarks BOTOX™ (Allergan, Inc., Irvine, Calif. U.S.A.) and DYSPORT™ (Speywood Pharmaceuticals, Ltd., Maidenhead, U.K.). The initial cosmetic use of BTX was for treatment of forehead frown lines as reported in J. Carruthers and A. Carruthers (1992) "Treatment of Glabellar Frown Lines with C. Botulinum-A Exotoxin"; J. Dermatol. Surge Oncol. 18: 17–21. Subsequently, various facial treatments employing BTX have been reported but use of BTX for treatment of midfacial defects has been limited.

Application of BTX near the mouth has been limited to treatment of neuromuscular disorder. For example, hemifacial spasm has been treated by BTX injection to the zygomaticus muscle but the modeolus adjacent the corner of the mouth is avoided (J. Carruthers and A. Carruthers (1996) Botulinum A Exotoxin in Clinical Ophthalmology; Can. J. Ophthalmol. 31: 389–400).

It has been reported that BTX injection to a group of muscles on one side of a patient's face has been used to treat facial synkinesis and vertical asymmetry caused by facial nerve palsy (Armstrong, M. W. J. et al. (1996) "Treatment of Facial Synkinesis and Facial Asymmetry with Botulinum Toxin Type A Following Nerve Palsy", Clin. Otolaryngol. 21:15–20). In the latter procedure, the levator anguli oris, zygomaticus major, rizorius and depressor anguli oris muscles associated with the mouth together with various muscles associated with the eye on the normal side of a patient's face were all treated as a group in order to affect the entire vertical symmetry of a patient's face to compensate for effects of nerve palsy on the untreated side of the face.

While BTX treatment of the platysma muscle has been performed for treatment of neck lines and banding, it has also been noted that injection of BTX into the platysma produces an uplift of the mouth (F. S. Brandt and B. Bellman (1998) Cosmetic Use of Botulinum A Exotoxin for the Aging Neck; Dermatol. Surg. 24: 1232–1234). Injection of BTX into the point of the chin has also been done for treatment of prominent mental crease (A. Carruthers and J. Carruthers; "Cosmetic Uses of Botulinum A Exotoxin"; In: James, W. D. et al Eds. Advances in Dermatology (1997) Mosby-Yearbook, Chicago: at pages 325–48).

The inventors have now found that "sad mouth" may be treated by simultaneous bilateral BTX injection to depressor anguli oris (triangularis) muscle (termed herein DAO) thereby affecting the horizontal symmetry of the mouth, without embarrassment to the appearance and function of the mouth. The normal function of the patient's lips is not impeded.

SUMMARY OF THE INVENTION

This invention provides the use of Botulinum toxin (BTX) to cause paralysis of a depressor anguli oris (DAO) musculature in a patient to alleviate downturn at corners of the patient's mouth.

This invention provides A method of alleviating downturn of corners of a patient's mouth comprising:

a) locating a depressor anguli oris (DAO) muscle adjacent each corner of said mouth; and b) injecting into a DAO adjacent each corner of the mouth, a quantity of Botulinum toxin (BTX) sufficient to cause paralysis of a DAO.

In this invention, BTX is simultaneously injected into each DAO adjacent each corner of the patient's mouth. By simultaneously, it is meant that the injection into each DAO occurs as part of the same treatment, although a DAO on one side of the mouth may be selected for injection before the other DAO during a treatment session.

DETAILED DESCRIPTION OF EMBODIMENTS OF THE INVENTION

Figure 1:
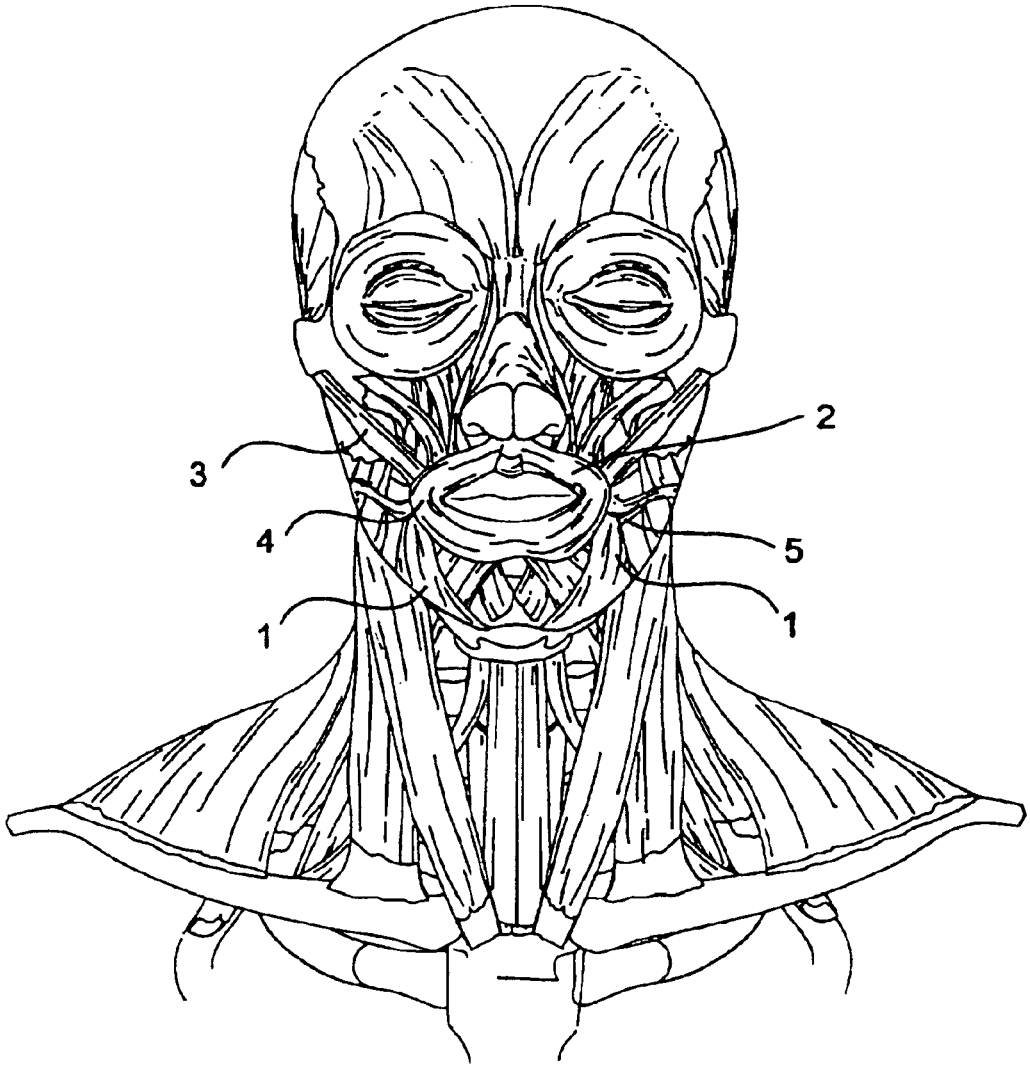
FIG. 1: is a frontal view showing musculature of the human face and neck.

The term "BTX" as used herein includes any neurotoxin produced by C. botulinum or derivatives thereof. Preferably, the neurotoxin will be the Botulinum-A exotoxin, termed herein "BTX-A".

The term "Unit equivalents" as used herein, is an amount of BTX which is equivalent to standard Units of BTX-A. A standard Unit of BTX-A is defined as the mean $LD_{50}$ for female Swiss Webster mice weighing 18–20 grams (E. J. Schantz and D. A. Kaultner (1978) Standardized Assay for Clostridium botulinum Toxins; J. Assoc. Anal. Chem. 61: 96–99). The estimated human $LD_{50}$(for a 70-kg person is 40 Units/kg or about 2500–3000 Units.

BOTOX™ is sold in 100 Unit vials, DYSPORT™ is sold in 500 Unit vials. For cosmetic uses, the vial contents are typically diluted 1 or 2 ml of with sterile saline solution, which for BOTOX™ provides a 100 or 50 Unit/ml dilution. DYSPORT™ BTX-A is roughly tenfold less toxic than BOTOX™ and approximately fourfold greater amounts of the DYSPORT™ product will usually be injected to achieve the same result as would is obtained using a specific number of Units of BOTOX™.

Commercially available toxin is typically freeze dried and is stored frozen (e.g. at −4° C.) until ready for use. The toxin is diluted just prior to use. The resulting solution should be used within several hours of preparation. Care should be taken to avoid foaming of the solution by slowing the entry of saline into the vacuum of the storage vial. The solution should not be shaken. Once used, remaining toxin, vial, needles and syringes should be disposed of in a manner appropriate for biohazardous waste.

Typical injection technique involves the use of a short, narrow needle (e.g. ½ inch or 8 mm; 30-gage) with an insulin of tuberculin type syringe. Patients are typically treated in the seated position. The skin area is cleaned with an alcohol swab. A single syringe may be used for multiple injections to treat different locations in a single muscle or different locations on a patient's face. Typically, the plunger of the syringe is depressed as the needle is withdrawn so that toxin is evenly distributed at the injection site. Pressure or gentle message may be applied at the injection site to assist in dissipating the toxin. The toxin will typically migrate approximately 1 cm from the site of injection.

Electromyographic (EMG) guided needles may be used for injection to determine needle location of a high degree of accuracy, although this technique is generally not necessary nor is it required in the instant invention.

In prior applications of BTX, total dose per treatment is variable and is largely dependent upon the condition being treated and the site of application of BTX. For example, a total dose of 20–30 Units will typically be applied to the glabellar complex and 60–75 Units for platysmal bands (c.f. A. Carruthers and J. Carruthers (1998) History of the Cosmetic Use of Botulinum A Exotoxin; Dermatol. Surg. 24: 1168–1170). Doses of up to 200 Units per treatment session for the platysma have been reported (Brandt and Bellman [supra]). In prior applications, a typical dose at a single injection point is approximately 5 Units of toxin in a 100 Unit/ml dilution.

Onset of muscle paralysis following injection usually occurs within hours of treatment. The duration of paralysis will vary from patient to patient. Typically, duration will be from 2–8 months before subsequent treatment is required to alleviate the condition.

This invention provides a successful treatment of Marionette lines and "sad mouth" by BTX injection into the DAO. In such treatment, the orbicularis oris muscle surrounding the mouth is normally avoided in view of its sensitivity to BTX. However, the orbicularis oris muscle may be treated in conjunction with this invention to alleviate severe upper lip lines or wrinkles. In such a case, a small amount of BTX is injected into the orbicularis oris, with the total dose being in the order of 4 Units for the entire upper lip. In general, care must be used in BTX treatments close to the mouth because of the danger of producing a flaccid cheek, an incompetent mouth, or an asymmetric smile.

The DAO may be found by instructing the patient to voluntarily and forcibly pull down the corners of the mouth. The DAO can be then felt by pulling inferiorly at a point approximately 1 cm lateral and 8 mm inferior to the commissure. Alternatively, EMG localization may be performed.

Treatment should take into consideration the pre-existing symmetry of the mouth and is performed on both sides of the face in order to provide a symmetric result. The required dosage to each side of the mouth should be judged and if necessary, altered upon re-treatment.

Injection may be made into any part of the DAO musculature. The injection is intramuscular and may be performed using the injection techniques used for other BTX treatments as described above. On a typical patient's face, the preferred point of injection into the DAO will be approximately 7 mm laterally and 8 mm inferior from the corner of the mouth. A single injection will usually suffice with the dosage for a single DAO muscle ranging from 3(±10%) Units–5(±10%) Units. The best dose will depend upon the sex of the patient and size of the individual. Typical doses for a female will be 2(±10%) Units–3(±10%) Units for one side of the mouth; and, for a male, 3(±10%) Units 5(±10%) Units for one side of the mouth.

Contraindications for the use of BTX are known in the art and include children under 12, pregnancy, lactation, history of neuromuscular disease and known sensitivity to BTX or human albumin. This invention is not be recommended for patients who are singers, musicians and other individuals who use their perioral muscles with intensity. However, treatment according to this invention will normally not affect normal speech, whistling or mastication particularly in cases where the orbicularis oris is not treated.

Following application of this invention, laser resurfacing techniques may be employed to enhance the effect. In the case of very deep Marionette lines, performance of this invention may be followed by soft tissue filling treatment such as collagen, Hylafor™, Restlyane™ (soft form) or Gore-Tex™ implants.

The drawings may be referred to for illustration of performance of this invention. FIG. 1 shows the location of various facial muscles and anatomical locations referred to herein, including: the DAO 1; orbicularis oris 2; zygomaticus 3; and, the modeolus 4. The platysma, which overlies the neck muscles and extends in part, to region 5, is not illustrated in FIG. 1.

Figure 2:
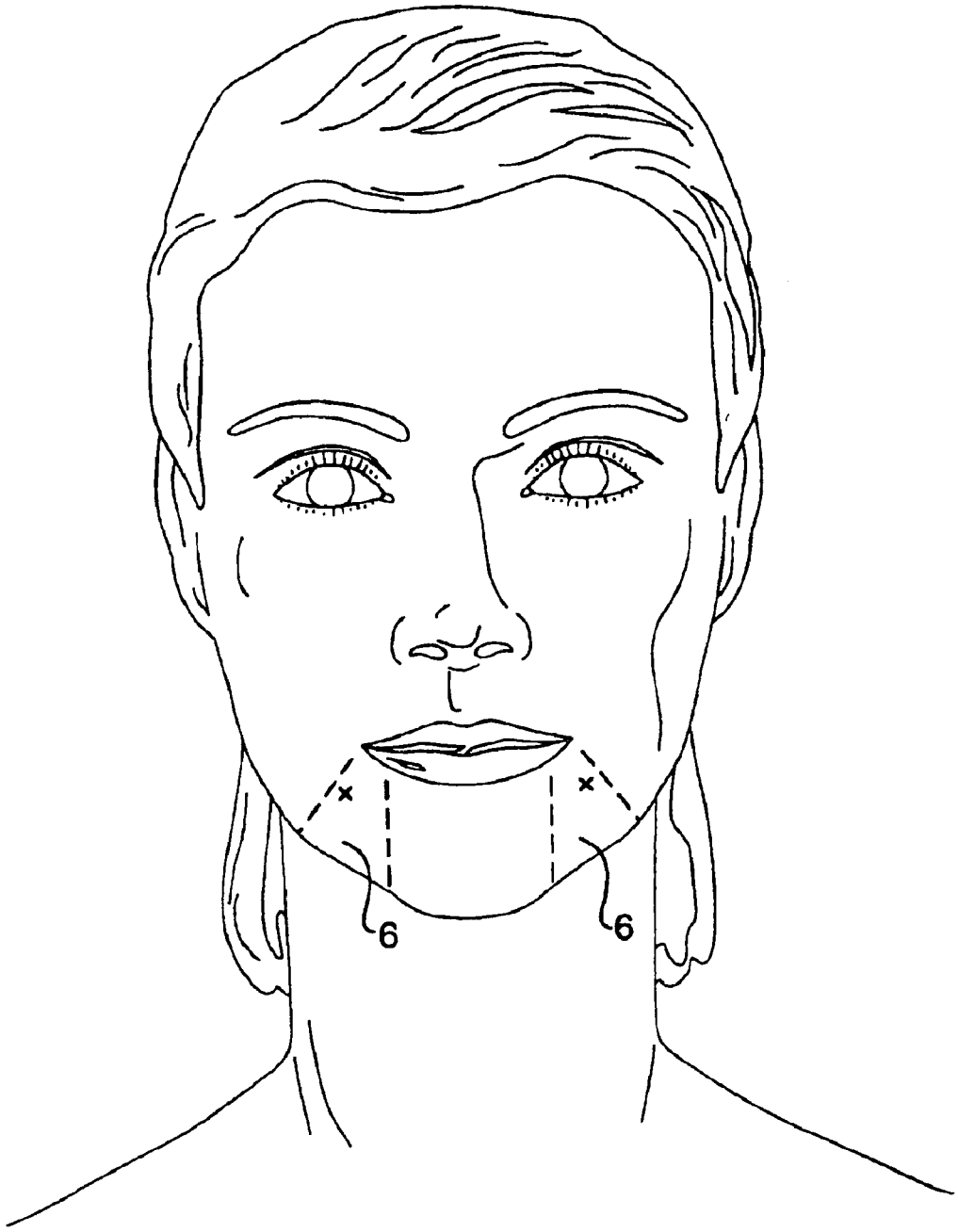
FIG. 2: is a front view of a human face and neck showing the general location of the DAO muscles and sites for BTX injection according to this invention.

In FIG. 2, region(s) 6 bounded by dashed lines illustrate the general location on the patient's skin which overly the DAO. Suitable injection sites include the areas within region (s) 6 that are marked with a "X".

All publications referred to herein are hereby incorporated by reference. While the following claims are intended to recite the features of the invention, it will be apparent to those of skill in the art that certain changes may be made without departing from the scope of this invention.

We claim:

1. A method of alleviating downturn of corners of a patient's mouth comprising:

[b)] locating a depressor anguli oris (DAO) muscle adjacent each corner of said mouth; and

[c)] injecting into a DAO adjacent each corner of the mouth, a quantity of [Botulnum] *Botulinum* toxin (BTX) sufficient to cause paralysis of a DAO.

2. The method of claim 1 wherein the quantity of BTX injected into each DAO is about 3–5 Unit equivalents.

3. The method of claim 2 wherein the BTX is Botulinum-A toxin.

4. The method of claim 1 wherein the quantity of BTX injected into each DAO is adjusted to compensate for symmetry of the mouth.

*5. A method for providing a facial cosmetic benefit to a human, comprising:*

*bilaterally injecting an amount of a Botulinum toxin to depressor anguli oris (DAO) muscles of a human patient, the amount of Botulinum toxin being effective to treat downturn of corners of a patient's mouth.*

*6. The method of claim 5, wherein the Botulinum toxin is Botulinum-A toxin.*

*7. The method of claim 5, wherein the Botulinum toxin is injected without being administered to the orbicularis oris muscle surrounding the mouth.*

*8. The method of claim 5, wherein the injection of Botulinum toxin is effective to alleviate wrinkles located near the mouth.*

*9. The method of claim 5, wherein the amount of Botulinum toxin is between about 2 units and about 5 units.*

*10. The method of claim 5, further comprising injecting an orbicularis oris muscle with a total dose of botulinum toxin in the order of 4 units for the entire upper lip.*

*11. The method of claim 5, further comprising locating a depressor anguli oris (DAO) muscle before injecting the Botulinum toxin.*

*12. The method of claim 5, further comprising a step of laser resurfacing tissue in proximity to the mouth.*

*13. The method of claim 5, further comprising a step of filling soft tissue in proximity to the mouth.*

*14. A method of alleviating severe upper lip wrinkles of a patient, comprising:*

*injecting a small amount of a botulinum toxin into the orbicularis oris muscle in proximity to an upper lip of a human afflicted with severe upper lip wrinkles in conjunction with a treatment of Marionette lines and sad mouth by injection of a botulinum toxin into each depressor anguli oris muscle, the total amount of the botulinum toxin being on the order of 4 Units for the entire upper lip, thereby alleviating the severe upper lip wrinkles.*

*15. The method of claim 14, wherein the Botulinum toxin is a botulinum-A toxin.*

*16. The method of claim 14, wherein the amount of botulinum toxin injected is at least about 2 units.*

*17. The method of claim 14, wherein the amount of botulinum toxin injected is at least about 3 units.*

*18. The method of claim 14, wherein the amount of botulinum toxin injected is in a range of about 2 units to about 5 units.*

*19. The method of claim 14, wherein the amount of botulinum toxin injected is in a range of about 3 units to about 5 units.*

*20. The method of claim 14, wherein only the orbicularis oris muscle in proximity to the upper lip is injected.*

*21. The method of claim 14, further comprising locating the DAO muscle before injecting the Botulinum toxin to the DAO muscle.*

*22. The method of claim 14, further comprising at least one step selected from the group consisting of laser resurfacing tissue in proximity to the mouth, and filling soft tissue in proximity to the mouth.*

*23. A method of alleviating downturn of corners of a patient's mouth comprising:*

*injecting into a depressor anguli oris (DAO) muscle adjacent each corner of the mouth, a quantity of Botulinum toxin sufficient to cause paralysis of a DAO.*

*24. The method of claim 23, wherein the botulinum toxin is Botulinum-A toxin.*

*25. The method of claim 23, wherein the quantity of Botulinum toxin is between about 2 units and about 5 units.*

*26. The method of claim 23, further comprising injecting on the order of 4 units of a Botulinum toxin to an upper lip region located above the patient's mouth.*

* * * * *